(12) United States Patent
Wang et al.

(10) Patent No.: US 8,176,795 B2
(45) Date of Patent: May 15, 2012

(54) APPARATUSES FOR PRESTRESSING ROD-TYPE SPECIMENS IN TORSION FOR IN-SITU PASSIVE FRACTURE TOUGHNESS TESTING IN AN EXTREMELY HIGH-PRESSURE ENVIRONMENT OF HYDROGEN

(75) Inventors: Jy-an Wang, Oak Ridge, TN (US); Ken C. Liu, Oak Ridge, TN (US); Zhili Feng, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 447 days.

(21) Appl. No.: 12/498,799

(22) Filed: Jul. 7, 2009

(65) Prior Publication Data

US 2011/0005331 A1    Jan. 13, 2011

(51) Int. Cl.
*G01N 3/02*    (2006.01)
*G01N 3/26*    (2006.01)

(52) U.S. Cl. ............................................. 73/856; 73/847

(58) Field of Classification Search ............ 73/847–848, 73/855, 856
See application file for complete search history.

(56) References Cited

U.S. PATENT DOCUMENTS

| | | | | |
|---|---|---|---|---|
| 4,601,198 A | * | 7/1986 | Kolitsch | 73/847 |
| 4,869,112 A | * | 9/1989 | Gram et al. | 73/856 |
| 5,083,471 A | * | 1/1992 | Ehret | 73/847 |
| 5,948,994 A | * | 9/1999 | Jen et al. | 73/856 |
| 6,289,744 B1 | * | 9/2001 | Larson et al. | 73/847 |

* cited by examiner

*Primary Examiner* — Lisa Caputo
*Assistant Examiner* — Jonathan Dunlap
(74) *Attorney, Agent, or Firm* — Luedeka Neely Group, P.C.

(57) ABSTRACT

An in-situ specimen fixture particularly adapted for prestressing rod-type SNTT-type specimens comprising a tube and end cap wherein the specimen is secured at one end to the tube, and at the opposite end to the end cap. The end cap is rotatable relative to the tube, and may be fixedly secured for creating a torsional force prestressing the specimen enclosed within the tube.

20 Claims, 4 Drawing Sheets

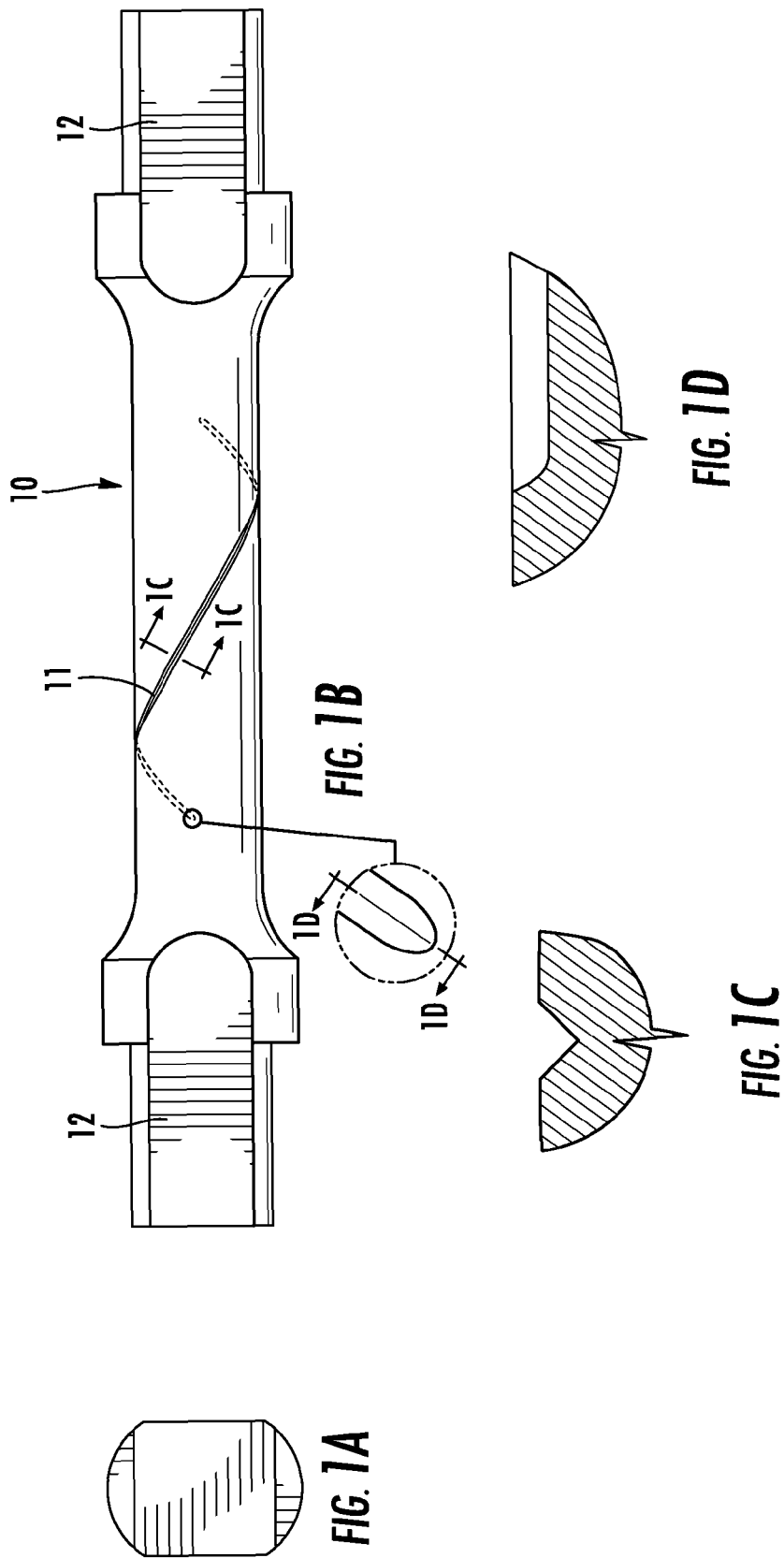

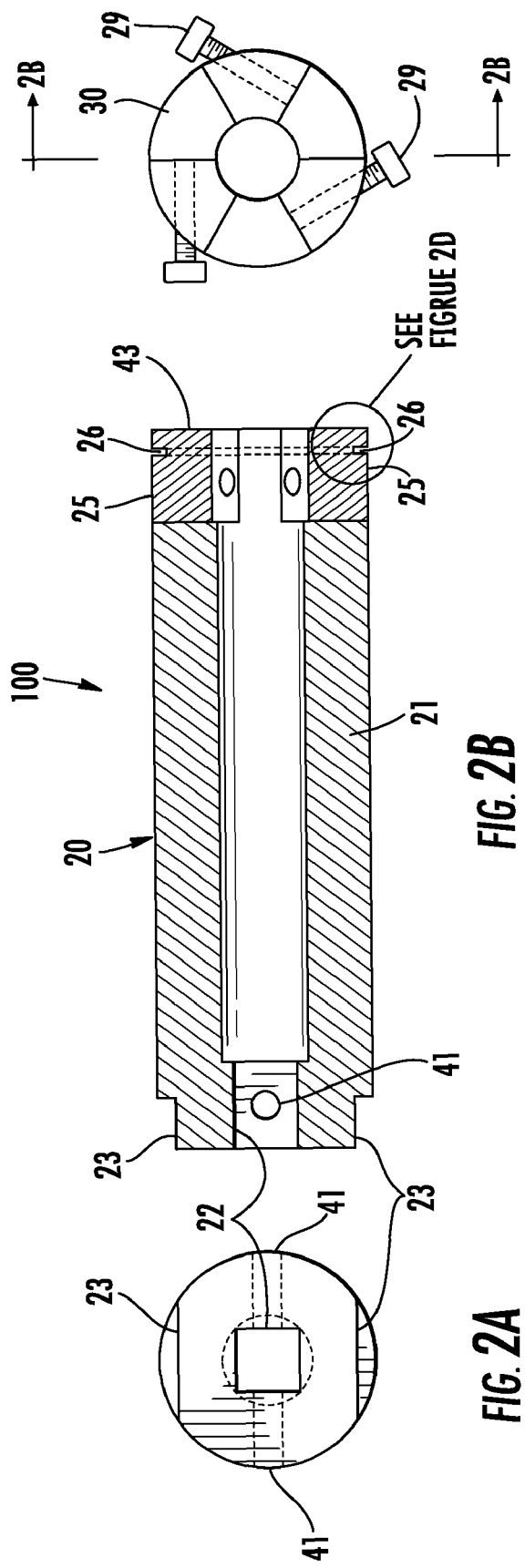

APPARATUSES FOR PRESTRESSING ROD-TYPE SPECIMENS IN TORSION FOR IN-SITU PASSIVE FRACTURE TOUGHNESS TESTING IN AN EXTREMELY HIGH-PRESSURE ENVIRONMENT OF HYDROGEN

GOVERNMENT RIGHTS

This invention was made with government support under Contract No. DE-AC05-00OR22725 awarded by the U.S. Department of Energy. The government has certain rights in the invention.

FIELD

This disclosure relates to the field of in-situ test specimen fixtures. More particularly, this disclosure relates to in-situ test specimen fixtures for rod-type Spiral Notch Torsion Test (SNTT)-type specimens.

BACKGROUND

Various methods of determining fracture toughness values of metallic and ceramic materials have been established by the American Society of Testing Materials (ASTM) and these standard methods are widely accepted by the technical community. Accordingly, a wealth of test data obtained by such protocols has been reported and evaluated for many types of these materials. In spite of the adherence to these standard methods, the test data obtained can still be scattered and inconsistent even within a family of the same material type, resulting in irreconcilable test data. Differences in the size of specimens, the inhomogenity of the specimen material and other inherent specimen factors which are not standardized can result in such inconsistencies.

Additional difficulties in determining fracture toughness occur when evaluating weldments, which inherently consist of three different phase zones: weld; heat affect; and base material. Each of these zones is likely to manifest a characteristically different microstructure and mechanical properties. As is well known, the fracture behavior of the fusion line that lies between the solidified weld puddle and the heat affect zone still remains unexplored because of the lack of a standardized test method.

Each of these difficulties is further complicated when evaluating the fracture toughness of these materials for use in high pressure hydrogen environments. Such information is important and needed for many energy development programs, yet the influences of hydrogen on in-situ crack behavior of weldments are virtually unknown. The standardized or conventional testing protocols previously mentioned are neither physically suitable nor economically viable for in-situ testing in extremely high pressure hydrogen environments. ASTM recommended compact tension (CT) specimens, and their variations, are generally tested in open space, and are not tailored for in-situ testing in a controlled environment with an extremely limited space such as that which occurs in many desired applications for these materials. Small and thin CT specimens do not yield reliable data and are not effective for use in investigating fracture toughness or fracture cracking behavior of weldments. Accordingly, a spiral-notch torsion test system (SNTT) was invented by Jy-An Wang and Kenneth C. Liu, "FRACTURE TOUGHNESS DETERMINATION USING SPIRAL-GROOVED CYLINDRICAL SPECIMEN AND PURE TORSIONAL LOADING", U.S. Pat. No. 6,588,283, the disclosure of which is hereby incorporated by reference, which utilizes a rod-type specimen having a helical groove with a 45-degree pitch to effectively simulate the fracture failure behavior of a thick CT specimen with a thickness equal to the total length of the groove line. This SNTT test method provides a small volume test specimen which is independent of the size effect previously encountered, and facilitates the testing of textured materials in any desired orientation.

SUMMARY

The present disclosure provides an in-situ specimen fixture particularly adapted for prestressing rod-type SNTT-type specimens comprising a tube and end cap wherein the specimen is secured at one end to the tube, and at the opposite end to the end cap. The end cap is rotatable relative to the tube, and may be fixedly secured for creating a torsional force prestressing the specimen enclosed within the tube.

In accordance with one embodiment, an in-situ test fixture includes a frame holding a test specimen, and a receiver disposed on a first frame end is configured for receiving a first end portion of the test specimen. The receiver also defines one end of a torsion axis and applies a torsion force to the test specimen about the torsion axis. A cap has an opening that is configured for receiving the second end portion of the test specimen and the cap also prevents rotation and applies a torsion force to the specimen. A rotational lock mechanism is formed on the cap and the second end of the frame for rotationally locking the end cap in a fixed rotational position relative to the second end of the frame. To apply and hold a desired torsion force, the specimen is inserted into the receivers on the frame and cap, and the cap is rotated about the torsion axis relative to the frame. When the desired torsion has been applied to the specimen, the end cap is rotationally locked relative to the frame to thereby hold a torsion force on the specimen. The frame and the specimen may both be placed in a desired environment such as a high pressure hydrogen environment for fracture testing.

The in-situ test fixture may also include a translational lock formed between the cap and the second end of the frame for locking the cap onto the frame and preventing translational movement between the cap and the frame, where translational movement is defined as movement parallel to the torsion axis. The translational lock may be a plunger mechanism formed in the end cap with a plunger that is extensible to an extended position and retractable to a retracted position. An indent may be formed in the second end of the frame, and it receives the plunger when the plunger is positioned in the extended position. The plunger in the indent locks the cap and frame together and prevents translational movement. When in the retracted position, the plunger disengages from the indent and allows translational movement between the cap and frame.

In particular, the plunger mechanism may be a threaded bore in the cap and the plunger may be a threaded bolt. The rotational lock may be a cap wedge formed on the cap and a frame wedge formed on the second end of the frame. The cap wedge is oriented oppositely from the frame wedge and is configured such that an abutment face of the cap wedge abuts an abutment face of the frame wedge to rotationally lock the cap on the second end of the frame.

BRIEF DESCRIPTION OF THE DRAWINGS

Various advantages are apparent by reference to the detailed description in conjunction with the figures, wherein elements are not to scale so as to more clearly show the details, wherein like reference numbers indicate like elements throughout the several views, and wherein:

FIGS. 1A-1D illustrates an SNTT specimen design configuration suitable for use in the in-situ test specimen fixture where FIG. 1A is an end view, FIG. 1B is a side view, FIG. 1C is a detailed view of a groove in the specimen, and FIG. 1D is a sectional view of the groove through section line 1D-1D;

FIGS. 2A-2D illustrates a torque applicator tube and cap of the in-situ test specimen fixture for receiving a test specimen where FIG. 2A is an end view of the tube, FIG. 2B is a side cross sectional view of the tube, FIG. 2C is an end view of the cap that fits on the end of the applicator tube, and FIG. 2D is a detail view of a groove in the tube;

FIG. 3 illustrates the end cap for the torque applicator tube of FIG. 2 whereby a predetermined torque is applied to the specimen for locking the specimen in permanent torsion where

DETAILED DESCRIPTION

In the following detailed description of a preferred embodiment, reference is made to the accompanying drawings, which form a part hereof, and within which are shown by way of illustration the practice of a specific embodiment of the in-situ test specimen fixture. It is to be understood that other embodiments may be utilized, and that structural changes may be made and processes may vary in other embodiments.

Referring now to FIG. 1, there is illustrated one embodiment of an SNTT specimen 10 for use in the in-situ fixture 100 to which a predetermined torsional force can be permanently applied for in-situ testing in, for example, an extremely high-pressure environment of hydrogen to test for hydrogen embrittlement. The specimen 10 has a spiral V-groove 11 formed on a uniform gage mid-section thereof, and squared end sections 12 for receiving in a manner hereinafter described.

Figure 3C:
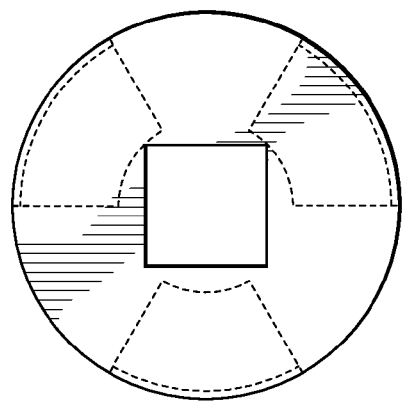
FIG. 3C is a view of the right end of the cap.
Figure 3B:
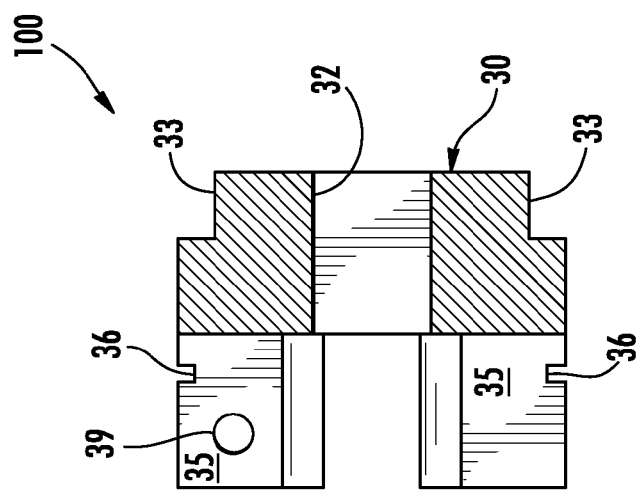
FIG. 3B is a side cross sectional view of the cap.
Figure 3A:
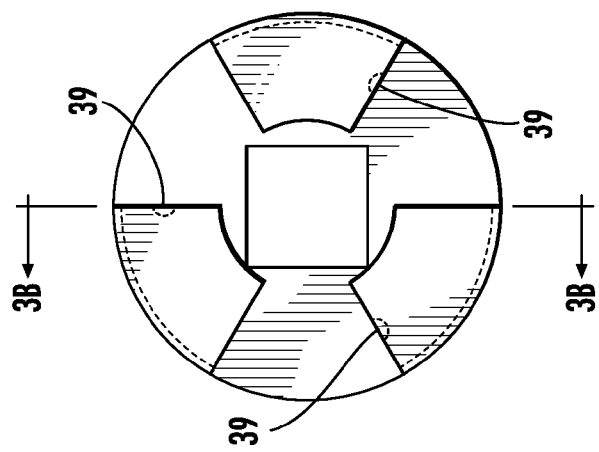
FIG. 3A is an left end view of the cap.

Referring to FIGS. 2 and 3 the in-situ fixture 100 comprises two portions, a heavy-walled tube 20 acting as a torque anchor, and an end cap 30 which is rotatable relative to the tube 20 to apply a torsional fracture force to a specimen 10 placed into the tube 20 and engaging the end cap 30. The tube 20 may be regarded as a frame; its primary function is to hold the specimen 10. In alternate embodiments an open frame may be used that does not necessarily enclose the specimen 10 and is not tubular.

The tube 20 is preferably made, for example, from a 0.55" ID by 1.25" OD high grade stainless steel tube 21 with a coaxial square hole 22 formed at one end. The hole 22 is sized for snuggly receiving one of the squared end sections 12 of the specimen 10. In this manner, once an end of the specimen 10 is inserted longitudinally through the tube 20 and into the square hole 22, the tube 20 acts as a torque anchor for the specimen 10. A pair of parallel flat portions 23 is formed in the tube wall adjacent to the square hole 22 for securing the tube 20 in a vise or the like.

The end of tube 20 opposite to the square hole 22 is castellated forming three 65 degree arc angle wedge sections 25 with a 55 degree arc angle space there between, as best illustrated in FIG. 2. Each of the three wedge sections 25 is formed with a threaded bore for receiving there through a threaded bolt 29 to lock the positioning of the tube 20 and end cap 30 after a torsional force has been applied to the specimen 10.

As best illustrated in FIG. 3, the end cap 30 is formed from the same steel as the tube 20, with a coaxial square hole 32 extending there through. The end cap hole 32 also is sized for snuggly receiving a squared end section 12 of the specimen 10 which will extend outwardly from the tube 20 beyond the castellated wedge portions 25 when seated in the square hole 22 formed in tube 20. In this manner, once one end of the specimen 10 is received into the square hole 22 of the tube 20, the other end of the specimen 10 will extend outwardly there from to be received into the end cap hole 32 of the end cap 30 so that a rotational force can be applied to the specimen 10. A matching complimentary set of three castellated wedge sections 35 is formed on the mating face of end cap 30, which in combination with the wedge sections 25 on the tube 20 can hold an applied torsional force to the specimen 10. The castellated wedge sections 25 and 35 may be considered a rotational lock because the wedge sections lock the end cap 30 against rotational movement relative to the tube 20. A suitable ring groove 26/36 is formed in the respective castellated wedge sections 25 and 35 so that when the end cap 30 has been placed on the tube 20, a "C" ring can be inserted into the grooves to secure the end cap onto the tube. A pair of parallel flat portions 33 is formed on the free end of the end cap 30, adjacent to the square hole 32, through which a rotational force can be applied to the end cap 30. Each of the castellated wedge sections 35 is formed with a spherical indent 39 which is to be engaged by the end of a respective bolt 29, threaded through the castellated wedge sections 25, to lock the relative rotational and translational position of the tube 20 and end cap 30.

Vents are provided in the tube 20 to allow the pressure inside and outside the tube 20 to equalize. In this embodiment, holes 41 are formed in the left side of the tube to allow gas to migrate into and out of tube 20, and a gap is formed between the face 43 of the tube 20 and the cap 30. The gap will likewise function as a vent between the inside and outside of the tube 20 when the specimen 10 is held in the tube 20.

Figure 4:
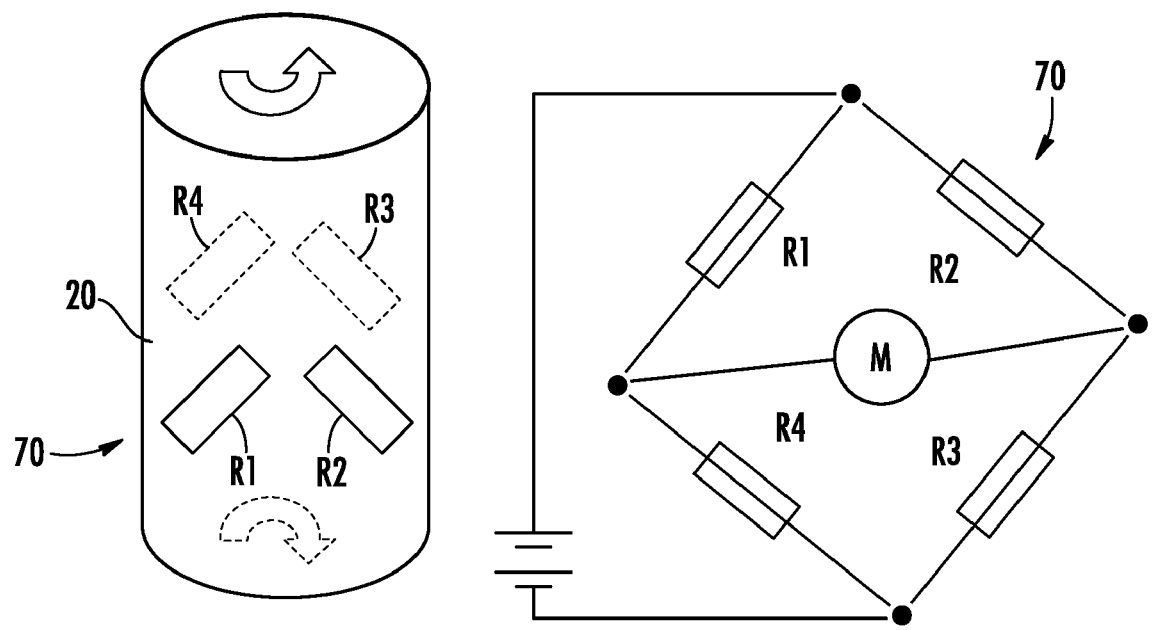
FIG. 4 is a schematic diagram of a full torsion bridge formed by four active strain gages on the in-situ test specimen fixture.

The amount of torsional force to be applied to the specimen 10 is monitored by the use of strain gauges, instrumented on the frame 20 or on the specimen 10. The full torsion bridge composed of R1, R2, R3 and R4 as illustrated in FIG. 4 is used on the frame 20. In this manner once the bridge on load frame 20 is calibrated, re-calibration for each tested specimen will not be necessary. While using a strain-gage full-bridge system on individual specimens also is suitable, such a bridge will require recalibration for each tested specimen. The illustrated four active strain gages R1, R2, R3 and R4 gages aligned in a torsion bridge on frame 20 eliminates the necessity for recalibration for each specimen. In operation the readings of voltmeter M are calibrated to correspond to the torsion applied to the tube. In this manner a torsional strain is developed in the specimen 10 by rotating the end cap 30 relative to the tube 20, the voltmeter M readings can be calibrated to provide a reading corresponding to the level of stress and strain on the specimen 10. The torsion force on the specimen 10 and the tube 20 will be the same, but in opposite directions. Thus by measuring stress or strain on either specimen 10 or tube 20, the stress and strain on either or both the specimen 10 and the tube 20 may be determined.

Referring again to FIGS. 1-3 the threaded bolts 29 in the castellated wedge sections 25 are tightened to bear against their respective indents 39 of the castellated wedge sections 35 to fixedly lock the relative rotational position between the tube 20 and end cap 30, and to set the stress and strain on the specimen 10. As the bolts 29 are rotated to extended positions, they engage the indents 39 and with continued rotation of the threaded bolts, the bolts will push against the indents and rotate the cap 30 relative to the tube 20 to thereby impose the desired torsion force on the specimen 20. The in-situ test specimen fixture 100 can impose a desired torsion stress and strain on a specimen 10 and then the complete fixture 100 can be placed in any desired environment for long term testing without requiring costly large-space testing facilities. In particular, the fixture may be disposed in high pressure hydrogen (e.g. 1,000 to 10,000 psi) and the specimens are thereby tested for fracture resistance under torsion stress-strain conditions.

The foregoing descriptions of embodiments have been presented for purposes of illustration and exposition. They are not intended to be exhaustive or to limit the embodiments to the precise forms disclosed. Obvious modifications or variations are possible in light of the above teachings. The embodiments are chosen and described in an effort to provide the best illustrations of principles and practical applications, and to thereby enable one of ordinary skill in the art to utilize the various embodiments as described and with various modifications as are suited to the particular use contemplated. All such modifications and variations are within the scope of the appended claims when interpreted in accordance with the breadth to which they are fairly, legally, and equitably entitled.

What is claimed is:

1. An in-situ test fixture for testing a specimen having first and second end portions, comprising:
    a tube for enclosing the test specimen to be prestressed in torsion;
    the tube including a closing end wall in which is defined an opening for receiving the first end portion of a test specimen enclosed therein, and further including an open end;
    a tube end cap rotatably engagable with the tube open end forming a rotatable closure for the tube open end;
    an opening formed in the tube end cap for receiving the second end portion of the test specimen enclosed in the tube;
    the tube end wall further including means for fixedly securing the end wall against rotational movement; and
    the tube end cap further including means for rotatably moving the tube open end relative to the tube end wall creating a torsional force prestressing the specimen enclosed therein.

2. The in-situ test fixture of claim 1 wherein the specimen is a spiral-notch torsion specimen.

3. The in-situ test fixture of claim 1 wherein the tube is formed as a cylinder.

4. The in-situ test fixture of claim 1 wherein the first end of the specimen has a polygon cross sectional shape and the opening in the tube end wall is formed with a shape that snuggly receives and engages the first end portion of a test specimen enclosed in the tube.

5. The in-situ test fixture of claim 1 wherein the tube open end is formed with a plurality of castellated wedges for engaging the end cap.

6. The in-situ test fixture of claim 5 wherein the end cap is formed with a plurality of castellated wedges complementary to the plurality of castellated wedges formed on the tube open end for engagement therewith.

7. The in-situ test fixture of claim 6 wherein each one of the plurality of castellated wedges includes means for securing the relative rotational position of the tube open end and the end cap.

8. The in-situ test fixture of claim 6 wherein each of the wedges is formed as a 65 degree arc angle with a 55 degree arc angle space therebetween.

9. The in-situ test fixture of claim 1 further comprising vents for balancing gas pressure inside and outside the tube when the specimen is mounted in the tube.

10. The in-situ test fixture of claim 1 further including means for fixedly securing the end cap to the open tube end in a predetermined rotational position.

11. An in-situ test fixture for applying and holding a torsion force about a torsion axis, the torsion for being applied to a test specimen having first and second end portions, comprising:
    a frame for holding a test specimen;
    the frame including a first frame end and a receiver disposed on the first frame end, the receiver being configured for receiving the first end portion of the test specimen, for defining one end of a torsion axis for preventing rotational motion of the specimen in the receiver about the torsion axis, and for applying a torsion force to the test specimen;
    the frame further including a second end distal from the first end;
    a cap fixed to the second end of the test specimen and rotatable with respect to the frame, the cap having an opening formed in the cap configured for receiving a second end portion of the test specimen for applying a torsion force to the specimen about the torsion axis;
    a rotational lock formed on the cap disposed and configured to apply a first force between the cap and the second end of the frame and thereby applies a torsion force to the test specimen, the rotational lock including a torsion adjustment mechanism that is movable in response to external forces so that movement of the torsion adjustment mechanism in one direction increases the first force and movement in a second direction decreases the first force, the rotational lock being configured for rotationally locking the end cap in a fixed rotational position relative to the second end of the frame in the absence of the external forces, the opening in the end cap when rotationally locked to the second end of the frame being disposed on the torsion axis whereby a torsion force may be constantly applied to the specimen when inserted into the frame and the cap in the absence of external forces, to thereby hold a torsion force on the specimen.

12. The in-situ test fixture of claim 11 further comprising a second lock formed between the cap and the second end of the frame for locking the cap onto the frame and preventing translational and rotational movement of the cap relative to the frame, where translational movement is defined as movement coaxial with the torsion axis and rotational movement is defined as rotation about the torsion axis.

13. An in-situ test fixture for applying and holding a torsion force about a torsion axis, the torsion for being applied to a test specimen having first and second end portions, comprising:
    a frame for holding a test specimen;
    the frame including a first frame end and a receiver disposed on the first frame end, the receiver being configured for receiving the first end portion of the test specimen, for defining one end of a torsion axis for preventing rotational motion of the specimen in the receiver about the torsion axis, and for applying a torsion force to the test specimen;
    the frame further including a second end distal from the first end;
    a cap having an opening formed in the cap configured for receiving a second end portion of the test specimen for applying a torsion force to the specimen about the torsion axis;

a rotational lock formed on the cap and the second end of the frame for rotationally locking the end cap in a fixed rotational position relative to the second end of the frame, the opening in the end cap when rotationally locked to the second end of the frame being disposed on the torsion axis whereby a torsion force may be constantly applied to the specimen when inserted into the frame and the cap, to thereby hold a torsion force on the specimen;

a second lock formed between the cap and the second end of the frame for locking the cap onto the frame and preventing translational and rotational movement of the cap relative to the frame, where translational movement is defined as movement coaxial with the torsion axis and rotational movement is defined as rotation about the torsion axis;

the second lock further comprising:

a plunger mechanism formed in the end cap, the plunger mechanism including a plunger that is extensible to an extended position and retractable to a retracted position, and an indent formed in the second end of the frame for receiving the plunger when positioned in the extended position and locking the cap and frame against translational movement and for releasing the plunger when in the retracted position to allow translational movement between the cap and frame.

14. The in-situ test fixture of claim 13 wherein the plunger mechanism comprises a threaded bore in the cap and the plunger comprises a threaded bolt.

15. An in-situ test fixture for applying and holding a torsion force about a torsion axis, the torsion for being applied to a test specimen having first and second end portions, comprising:

a frame for holding a test specimen;

the frame including a first frame end and a receiver disposed on the first frame end, the receiver being configured for receiving the first end portion of the test specimen, for defining one end of a torsion axis for preventing rotational motion of the specimen in the receiver about the torsion axis, and for applying a torsion force to the test specimen;

the frame further including a second end distal from the first end;

a cap having an opening formed in the cap configured for receiving a second end portion of the test specimen for applying a torsion force to the specimen about the torsion axis;

a rotational lock formed on the cap and the second end of the frame for rotationally locking the end cap in a fixed rotational position relative to the second end of the frame, the opening in the end cap when rotationally locked to the second end of the frame being disposed on the torsion axis whereby a torsion force may be constantly applied to the specimen when inserted into the frame and the cap, to thereby hold a torsion force on the specimen;

wherein the rotational lock comprises:

at least one abutment face formed on the cap;
at least one abutment face formed on the frame; and
the abutment faces on the cap and frame being configured and positioned to abut one another and prevent rotational movement of the cap relative to the frame about the torsion axis when the cap is rotationally locked on the frame.

16. The in-situ test fixture of claim 15 wherein the rotational lock further comprises:

at least one cap wedge formed on the cap and having an inclined face;
at least one frame wedge formed on the second end of the frame and having an inclined face, the cap wedge being oriented oppositely from the frame wedge and being configured such that the abutment face of the cap wedge abuts the abutment face of the frame wedge to rotationally lock the cap on the second end of the frame.

17. A method of imposing a fixed torsional force on a test specimen for in-situ testing of the test specimen while fixedly connected to a test fixture comprising a test frame member and a cap member, the steps including:

securing a first end of a double-ended test specimen to a test frame member of a test fixture;
said double-ended test specimen having a second end distally spaced from said first end to define a test specimen torsion axis;
securing the second end of the double-ended test specimen to a cap member of the test fixture;
said cap member being spaced from said test frame member along the test specimen torsion axis;
securing said cap member to said test frame member to prevent relative movement there between along the test specimen torsion axis;
applying a relative rotational movement between said test frame member and said cap member and second end of the test specimen fixed thereto in response to external forces in a plane normal to the test specimen torsion axis by rotating the cap member relative to the test frame member and thereby applying a first force between the cap member and the test frame member;
measuring the torsional strain on the test frame member for determining the torsional force being applied to the test specimen, and
maintaining the relative rotational position of the test frame and cap members upon the application of a determined torsional force to the test specimen to maintain the test specimen under the determined torsional force for in-situ testing of the test specimen while fixedly positioned between the test frame and cap members of the test fixture.

18. A method of imposing a fixed torsional force on a test specimen for in-situ testing of the test specimen while fixedly connected to a test fixture comprising a test frame member and a cap member, the steps including:

securing a first end of a double-ended test specimen to a test frame member of a test fixture;
said double-ended test specimen having a second end distally spaced from said first end to define a test specimen torsion axis;
securing the second end of the double-ended test specimen to a cap member of the test fixture;
said cap member being spaced from said test frame member along the test specimen torsion axis;
securing said cap member to said test frame member to prevent relative movement there between along the test specimen torsion axis;
applying a relative rotational movement between said test frame member and said cap member in a plane normal to the test specimen torsion axis by rotating the cap member relative to the test frame member;
measuring the torsional strain on the test frame member for determining the torsional force being applied to the test specimen, and
maintaining the relative rotational position of the test frame and cap members upon the application of a determined torsional force to the test specimen to maintain the test specimen under the determined torsional force for in-situ testing of the test specimen while fixedly positioned between the test frame and cap members of the test fixture;

wherein the step of rotating the cap member relative to the test frame member comprises rotating at least one of a plurality of lead screws carried by the cap member in operative engagement with the test frame member to effect the rotational movement thereof.

19. The method of claim 18 wherein the step securing the cap member to the test frame member to prevent movement there between along the test specimen torsion axis comprises positioning a "C" ring into aligned grooves formed in the cap member and the test frame member to lock the lateral position there between.

20. The method of claim 18 wherein the step of maintaining the relative rotational position of the test frame and cap members upon the application of a determined torsional force to the test specimen to maintain the test specimen under the determined torsional force for in-situ testing of the test specimen while positioned between the test frame and cap members of the test fixture comprises securing each one of a plurality of lead screws carried by the cap member in operative engagement with the test frame member to fix the rotational movement thereof upon the application of the predetermined torsional force to the test specimen.

* * * * *